United States Patent [19]

Rasmussen

[11] 4,285,948
[45] Aug. 25, 1981

[54] N-ARYL-N'-(1,4,5,6-TETRAHYDROPYRIMIDINE-2-YL)UREAS AS ANTIHYPERTENSIVES

[75] Inventor: Chris R. Rasmussen, Ambler, Pa.

[73] Assignee: McNeilab, Inc., Fort Washington, Pa.

[21] Appl. No.: 159,988

[22] Filed: Jun. 16, 1980

[51] Int. Cl.³ .................. A61K 31/505; C07D 239/02
[52] U.S. Cl. ..................................... 424/251; 544/332
[58] Field of Search ......................... 424/251; 544/332

[56] References Cited

U.S. PATENT DOCUMENTS 3,759,921  9/1973  Paget .................................... 424/251

OTHER PUBLICATIONS

Douglas et al., Arzneim.-Forsch./Drug Res. 28 (II), Heft 8a, (1978).

*Primary Examiner*—Frank Cacciapaglia, Jr.

[57] ABSTRACT

A process for controlling hypertension employing N-(substituted-phenyl)-N'-(1,4,5,6-tetrahydroprimidin-2-yl)ureas, and pharmaceutical compositions containing said ureas is described.

6 Claims, No Drawings

N-ARYL-N'-(1,4,5,6-TETRAHYDROPYRIMIDINE-2-YL)UREAS AS ANTIHYPERTENSIVES

FIELD OF INVENTION

This invention relates to a method for controlling hypertension employing certain N-aryl-N'-(1,4,5,6-tetrahydropyrimidin-2-yl)ureas and to pharmaceutical compositions containing said urea compounds.

BRIEF SUMMARY OF THE INVENTION

The present invention involves a method of reducing arterial pressure in hypertensive animals by administering to a hypertensive subject, in a pharmaceutically-acceptable carrier, a therapeutically-effective amount of a compound, or a pharmaceutically-acceptable salt thereof, having the formula:

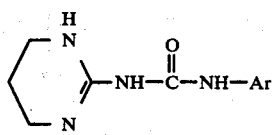

In the foregoing and subsequent formulas, Ar is a phenyl radical of the formula:

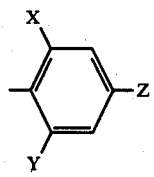

wherein X and Y are each independently selected from the group consisting of H, Br, Cl, F, $CH_3$, $CF_3$, or $OCH_3$; and Z is H or F.

The very most preferred compounds, for use as antihypertensives are those above wherein X and Y are each independently selected from the group consisting of Br, Cl, $CH_3$ and $CF_3$; and Z is H.

This invention also embraces compositions, suitable for use in the above antihypertensive method, wherein the foregoing urea compound is in admixture with a pharmaceutically acceptable carrier. The most preferred composition contains the compound wherein X and Y are each Cl and Z is H, which is the most active antihypertensive compound, or its pharmaceutically-acceptable salts.

The activities of the above compounds reside in the urea base so that useful acid addition salts may be from various acids provided only that the acids be pharmaceutically-acceptable. Representative acid salts include hydrochloride, hydrobromide, phosphate, sulfate, p-toluenesulfonate, benzenesulfonate, malonate, succinate, methosulfate, methanesulfonate, 2-napsylate and the like.

PRIOR ART

Certain N-(aryl)-tetrahydropyrimidin-2-yl ureas are generically disclosed in U.S. Pat. No. 3,168,520, but the only utility taught is in connection with dyeing, and no pharmaceutical utility is taught, nor is any of the compounds used in the present invention specifically disclosed.

An article by G. H. Douglas, et al., *Arzneimittel Forschung.*, Vol. 28 (II) Supplement 8a, 1435–1441 (1978) discloses as Compound 109 at p. 1438 (in its tautomeric form) the compound of the formula:

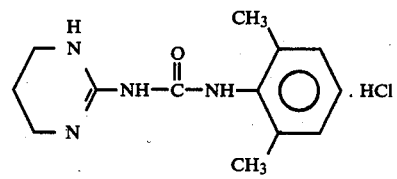

which was disclosed to be active as a gastric acid antisecretory agent. The article does not teach the antihypertensive activity for this 2,6-dimethylphenyl compound, which applicant found to exist.

METHOD OF PREPARATION

The pharmacologically useful N-aryl-N'-(1,4,5,6-tetrahydropyrimidin-2-yl)urea compounds are prepared from 2-amino-1,4,5,6-tetrahydropyrimidine-HCl, which has the structure:

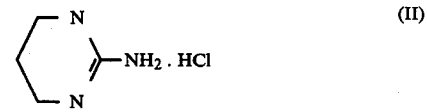

and which is a known compound (R. F. Evans and D. J. Brown, J. Chem. Soc., 4039 (1962) prepared according to the following reaction scheme:

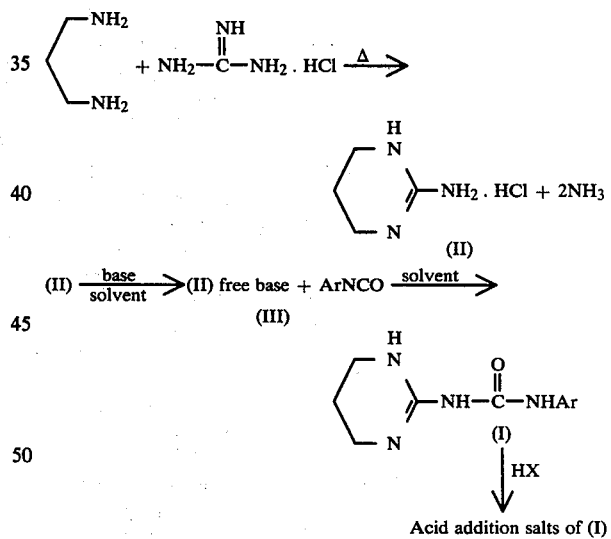

The free base form of II can be generated by treating a stirring suspension of II HCl in solvents such as $CH_2Cl_2$ (methylene chloride), tetrahydrofuran, dioxane, and the like with strong bases such as aqueous NaOH (50%), concentrated KOH, and the like; NaOH (50%) being preferred. The resulting solution of free base II is dried over a suitable drying agent such as $Na_2SO_4$ or $K_2CO_3$. The dried solutions may either be used as such for reactions with aryl isocyanates to obtain products I or the extraction solvent may be evaporated in vacuo and the residual free base II taken up in a different organic solvent, e.g., DMF, DMSO, and the like; said solutions of II then being treated with an appropriate isocyanate III to afford the free base products I. Although the reactions of II with III may be carried out with equimolar amounts of reactants, usually a stoichiometric excess, generally of from about 0.25–1.0 mole of free base II to that of aryl isocyanate III is employed in order to minimize undesired side reactions such as, for example, formation of bis-aryl isocyanate adducts with II. Temperature ranges for those reactions may conveniently range from about −20° to 70° C. The products I, obtained in free base form, may conveniently be purified by dissolving in an organic solvent, immiscible with H$_2$O, such as CH$_2$Cl$_2$, washing with H$_2$O to remove excess II if any followed by isolation of I from the solvent by drying, filtration from drying agent, and solvent removal.

Alternatively, the reactions of II free base with III may be carried out by adding a solution of II HCl in DMF, DMSO, and the like, to a stirring suspension of a stoichiometric amount of an alkali metal hydride such as LiH, NaH, and the like, LiH being preferred, which forms II free base, the corresponding alkali metal chloride, and H$_2$ gas.

The thus obtained solution of free base II (the presence of the metal chloride does not interfere with the subsequent reaction) is treated with an appropriate amount of aryl isocyanate III. When the reaction is complete, dilution with H$_2$O or ice-H$_2$O, in excess amounts, causes precipitation of crude product I and leaves any unreacted II in solution. Filtration then allows isolation of crude I.

Said I, in free base form, may be further purified, if necessary, by recrystallization and chromatographic techniques, and so forth, according to standard techniques known in the art. A further purification method may be used such as dissolution in dilute aqueous acid, such as HCl, most preferred, H$_2$SO$_4$, HBr, HNO$_3$ and the like, filtration from any undissolved impurities, followed by neutralization with suitable inorganic bases such as sodium and potassium bicarbonates and carbonates and the like, dilute alkali metal hydroxides such as NaOH, KOH, and the like, and organic bases such as triethylamine, diisopropylethylamine, and the like, which causes precipitation of I free base. The thus-obtained free base I may then be purified by recrystallization, etc., as described above, or may be converted to a suitable pharmaceutically-acceptable salt form of I which also may be purified by recrystallization or precipitation techniques well known in the art.

Said pharmaceutically-acceptable salt forms of I are generally comprised of I in combination with suitable mineral acids such as HCl (most preferred), HBr, H$_2$SO$_4$, H$_3$PO$_4$, and strong organic acids such as benzenesulfonic, p-toluenesulfonic, 1- and 2-naphthalenesulfonic, ethanedisulfonic, methane- and ethanesulfonic methylsulfuric, and the like, being the most preferred. Although salts of I with weaker acids, such as benzoic, fumaric, maleic, citric, etc. do form, they are relatively easily dissociated because of the relatively weak base strength of I. This dissociation may be caused by attempted drying in vacuo, dissolution in H$_2$O, etc. The ease of dissociation, however, may not necessarily preclude use of salts of this type in pharmaceutical formulations insofar as they remain stable enough to be purified by recrystallization, etc., and capable of being formulated into pharmaceutical preparations such as tablets, capsules, and the like.

The preferred salt forms of I are additionally capable of forming hydrates and solvates with H$_2$O and certain organic solvents, respectively. Also, I and its salt forms may exist in several tautomeric forms. It is naturally intended that the various hydrates, solvates, and tautomeric forms of I be included within the scope of this invention.

The N-(substituted phenyl)-N'-(1,4,5,6-tetrahydropyrimidin-2-yl)urea compounds useful in the present invention have been found to alleviate hypertension and further, to generally accomplish this without an accompanying increase in heart rate. The compounds most useful in the present invention do not show an increase in heart rate, but a lowering of heart rate and, generally, long duration. An agent which has an antihypertensive effect without increasing but rather maintaining or decreasing heart rate, is the one considered most useful for beneficially treating a hypertensive subject. The extent to which a compound possesses these properties may be primarily determined in the antihypertensive test hereinafter described.

Rodent Antihypertensive Screen—This test evaluates compounds for effects on arterial pressure and heart rate. In this test, the arterial pressure of adult spontaneously hypertensive rats [SHR] (Charles River) is monitored directly via an aortic cannula. Rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cases and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control.

The results of this test employing at least 3 rats per dose level for each compound and performed with N-aryl-N'-(1,4,5,6-tetrahydropyrimidin-2-yl))urea compounds are shown in Table I.

The results seen in Table I show that N-(substituted phenyl)-N'-(1,4,5,6-tetrahydropyrimidin-2-yl)urea compounds and their salts possess not only the beneficial antihypertensive property but also the desirable property of maintaining or lowering heart rate.

The compounds used in the present invention are useful for treating hypertension (high blood pressure) by administering to subjects in need of treatment, a therapeutically-effective hypertension reducing amount of a N-(substituted phenyl)-N'-(1,4,5,6-tetrahydropyrimidin-2-yl)urea compound of Formula I or its pharmaceutically-acceptable salt as active agent. The active agents may be administered with or without carrier in the amounts hereinafter set forth. A preferred method of administration is by the use of pharmaceutical compositions in unit dosage form as described below.

The operable ranges for carrying out the treatment is the administration, orally or parenterally, of from about 1 milligram to about 500 milligrams of said N-(substituted phenyl)-N'-(1,4,5,6-tetrahydropyrimidin-2-yl)urea compound in dosage unit form. While the therapeutic method is most useful for human subjects, it may also be employed for other mammals. Operable amounts are generally within the range of from about 0.5 to 100 mg/kg of body weight.

TABLE I
ANTIHYPERTENSIVE AND CARDIAC RATE DETERMINATIONS $$\begin{array}{c} H \\ N \\ \diagdown \\ \diagup\text{—NHCNHAr . HCl .} \frac{1}{4}H_2O \\ N \\ \end{array}$$

| | | | SHR Rat | | |
|---|---|---|---|---|---|
| Ar | McN- | -/- | Map in Δmm Hg (mg/kg,route) | Δ HR in beats/ min. | Duration in hours |
| 2,6-Cl$_2$Ph | 4951(base) | — | −54 (35 p.o.) | −86 | 21 |
| 2,6-Cl$_2$Ph | 4951(base) | — | −79 (100 p.o.) | −114 | >24 |
| 2,6-Cl$_2$Ph | 4951(base) | — | −58 (30 p.o.) | −140 | >24 |
| 2,6-Cl$_2$Ph | 4951(base) | — | −78 (30 i.p.) | −100 | >24 |
| 2,6-Cl$_2$Ph | 4951(base) | — | −41 (10 p.o.) | −76 | >24 |
| 2,6-Cl$_2$Ph | 4951(base) | — | −42 (3 p.o.) | −36 | 17 |
| 2,6-Cl$_2$Ph | 4951(base) | — | −24 (1 p.o.) | −44 | 1 |
| 2-CF$_3$Ph | 5027-11-98 | 1 | −49 (30 i.p.) | −110 | 11 |
| | | | −65 (100 p.o.) | −74 | 11 |
| 2,6-Me$_2$Ph art compound | 5028-11-98 | 1.1 | −70 (30 i.p.) | −126 | 23 |
| | | | −82 (100 p.o.) | −168 | >24 |
| 2-Cl-6-MePh | 5058-11-98 | 0.5 | −73 (30 i.p.) | −103 | >24 |
| | | | −66 (100 p.o.) | −118 | >24 |
| 2,6-Br$_2$-4-FPh | 5042-11 | 0 | −90 (30 i.p.) | −60 | 17 |
| | | | −37 (100 p.o.) | −71 | 11 |

MAP = Mean Arterial Pressure
Δ = Change
HR = Heart Rate

Pharmaceutical compositions containing the N-(substituted phenyl)-N'-(1,4,5,6-tetrahydropyrimidin-2-yl)urea compounds of the present invention or acid addition salt thereof, as the active ingredient, may be prepared by intimately mixing the urea compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof. A dosage unit generally will contain from about 1 to about 500 mg of the N-(substituted phenyl)-N'-(1,4,5,6-tetrahydropyrimidin-2-yl)urea compound.

The following examples illustrate the preparation of the N-(substituted phenyl)-N'-(1,4,5,6-tetrahydropyrimidin-2-yl)urea compounds and the novel pharmaceutical compositions suitable in the practice of the invention but are not to be construed as limiting:

EXAMPLE I-A

N-(2,6-Dichlorophenyl)-N'-(1,4,5,6-tetrahydropyrimidin-2-yl)urea

A solution of 4.20 g (0.0424 mol) of 2-aminotetrahydropyrimidine in 30 ml of dry DMF was warmed to 70° C. and with stirring was added 7.16 g (0.0381 mol) of 2,6-dichlorophenyl isocyanate in 25 ml of dry DMF over a period of 0.5 hours. After stirring for 2 hours at 70° C., the reaction mixture was cooled, diluted with H$_2$O and filtered. The filter cake was washed well with H$_2$O and air dried. The crude product, 5.1 g (47%) was dissolved in CH$_2$Cl$_2$, dried over K$_2$CO$_3$, filtered through a prewashed pad of filter aid and hexane was added to the cloud point. The resulting crystals were filtered, washed with hexane and dried in vacuo for 3 hours (50° C.; 5 mm Hg) to give pure N-(2,6-dichlorophenyl)-N'-(1,4,5,6-tetrahydropyrimidin-2-yl)urea, 4.71 g (43%); m.p. 179°-180.5° C. TLC: 5×20 cm silica gel; toluene-ether-MeOH (8:4:1) or CHCl$_3$-MeOH-NH$_4$OH (90:10:1) indicated homogeneity; IR (KBr) 3421,1628 cm$^{-1}$; UV max. (MeOH) 222 nm ($\epsilon$=28300) and 239 nm (inflection) ($\epsilon$=18,000).

ANAL. Calcd. for C$_{11}$H$_{12}$Cl$_2$N$_4$O: C, 46.01; H, 4.21; N, 19.51. FOUND: C, 45.98; H, 4.23; N, 19.48.

The starting 2-aminotetrahydropyrimidine was prepared according to the procedure of R. F. Evans, D. J. Brown, *J. Chem. Soc.*, 4039 (1962), which was liberated from the hydrochloride with excess 50% NaOH, extracted with CH$_2$Cl$_2$, dried (K$_2$CO$_3$) and evaporated in vacuo to an oil.

EXAMPLE I-B

N-(2,6-Dichlorophenyl)N'-(1,4,5,6-tetrahydropyrimidin-2-yl)urea Monohydrochloride A mixture of 8.50 g (0.0625 mol) of 2-amino-1,4,5,6-tetrahydropyrimidine hydrochloride, 10.0 g (0.12 mol) of 50% NaOH and 70 ml of THF was stirred for 0.5 hours at room temperature and then 10.0 g Na$_2$SO$_4$ was added. After stirring for an additional 0.5 hours, a solution of 9.4 g (0.050 mol) of 2,6-dichlorophenyl isocyanate in 50 ml of THF was added over a period of 1 hour. After stirring for 1 hour, the reaction mixture was filtered, the filtrate evaporated in vacuo and the residue dissolved in 25 ml of 10% HCl and 25 ml of H$_2$O with warming. After filtration through a pad of diatomaceous earth, chilling in ice gave the crystalline hydrochloride which was recrystallized from MeOH-ether affording 12.40 g. This material was ground to a fine powder and dried to constant weight in vacuo (60° C., 5 mm Hg) to give 11.97 g (74%) of the title compound; m.p. 215°-217° C. dec., homogeneous by TLC [5×20 cm silica gel GF CHCl$_3$—MeOH—NH$_4$OH (90:9:1)]. $^1$H-NMR (DMSO-d$_6$) 1.85 [pentet, (poorly resolved)2 H]; 3.35 (t, J=5 HZ, 4 H); 7.2-7.7 (m, 3 H); 9.16 (broad s, 2 H) exchangeable; 10.02 (broad s, 1 H) exchangeable; 11.19 (broad s, 1 H) exchangeable. IR(KBr) 3125, 1717, 1678, 1628 cm$^{-1}$.; UV max. (MeOH) 241 infl. ($\epsilon$=11,200) and 220 nm infl. ($\epsilon$=23,500).

ANAL. Calcd. for $C_{11}H_{12}Cl_2N_4O·HCl$: C, 40.83; H, 4.05; N, 17.31. FOUND: C, 40.78; H, 4.05; N, 17.30.

EXAMPLE II

N-(1,4,5,6-tetrahydropyrimidin-2-yl)-N'-(2-trifluoromethylphenyl)urea Monohydrochloride Hydrate A mixture of 9.90 g (0.073 mol) of 2-amino-1,4,5,6-tetrahydropyrimidine hydrochloride, 6.0 g (0.075 mol) of 50% NaOH and 75 ml of THF was stirred for 0.75 hours at room temperature and then 10 g. $Na_2SO_4$ was added. After stirring for 0.5 hours, a solution of 9.36 g. (0.050 mol) of methyl-2-trifluoromethylphenyl isocyanate in 50 ml of THF was added over a period of 0.5 hours. After stirring for 1 hour, the reaction mixture was filtered, the filtrate evaporated in vacuo and the residue dissolved in 50 ml of 10% HCl and 100 ml of $H_2O$ with warming. After filtration through a pad of diatomaceous earth, chilling in ice gave the crystalline hydrychloride which was recrystallized from hot $H_2O$ affording 10.09 g (63%). This material was dried to constant weight in vacuo (20° C., 5 mm Hg) to give pure N-(1,4,5,6-tetrahydropyrimidin-2-yl)-N'-(2-trifluoromethylphenyl)urea monohydrochloride hydrate; m.p. (120) 182.5°–184.5° C. $IR(CHCl_3)$ 3240 (br), 1717, 1642, 1594 cm$^{-1}$. UV max. (MeOH) 281 infl ($\epsilon$6,900), 256 nm ($\epsilon$29,000) and 215 nm ($\epsilon$14,900).

ANAL. Calcd. for $C_{12}H_{13}F_3N_4O·HCl·H_2O$: C, 42.30; H, 4.73; N, 16.44; $H_2O$, 5.29. FOUND: C, 42.40; H, 4.78; N, 16.24; $H_2O$, 5.18.

EXAMPLE III

N-(2,6-Dimethylphenyl)-N'-(1,4,5,6-tetrahydropyrimidin-2-yl)urea Monohydrochloride Hydrate (10:10:11)

A mixture of 8.13 g (0.060 mol) of 2-amino-1,4,5,6-tetrahydropyrimidine hydrochloride, 5.0 g (0.0625 mol) of 50% NaOH and 75 ml of THF was stirred for 0.5 hours at room temperature and then 10.0 g $Na_2SO_4$ was added. After stirring for 0.5 hours, a solution of 5.89 g (0.040 mol) of 2,6-dimethylphenyl isocyanate in 50 ml of THF was added over a period of 0.5 hours. After stirring for 1 hour, the reaction mixture was diluted with 100 ml of $CH_2Cl_2$, filtered, the filtrate evaporated in vacuo and the residue dissolved in 25 ml of 10% HCl and 50 ml of $H_2O$ with warming. After filtration through a pad of diatomaceous earth, chilling in ice gave the crystalline hydrochloride which was recrystallized from cold $H_2O$ affording 8.78 g (55%). This material was dried in vacuo (20° C., 5 mm Hg) to constant weight giving N-(2,6-dimethylphenyl)-N'-(1,4,5,6-tetrahydropyrimidin-2-yl)urea monohydrochloride hydrate (10:10:11); m.p. (110) 214.5°–216.5° C. dec.; IR $(CHCl_3)$ 3226, 1710, 1676, 1641 cm$^{-1}$. UV max. (MeOH) 270 shl ($\epsilon$1,000) and 233 nm ($\epsilon$18,300).

ANAL. Calcd. for $C_{13}H_{18}N_4O·HCl·1.1 H_2O$: C, 51.60; H, 7.06; N, 18.52; $H_2O$, 6.55. FOUND: C, 51.68; H, 7.23; N, 18.53; $H_2O$, 6.49.

EXAMPLE IV

N-(2,6-Dibromo-4-fluorophenyl)-N'-(1,4,5,6-tetrahydropyrimidin-2-Yl)urea Monohydrochloride A mixture of 8.14 g (0.060 mol) of 2-amino-1,4,5,6-tetrahydropyrimidine hydrochloride, 6.0 g (0.075 mol) of 50% NaOH and 75 ml of THF was stirred at room temperature for 0.5 hours and then 10.0 g $Na_2SO_4$ was added. After stirring for 0.5 hours, a solution of 11.8 g (0.040 mol) of 2,6-dibromo-4-fluorophenyl isocyanate in 70 ml of THF was added over a period of 0.75 hours. After stirring for an additional 2 hours, the product THF suspension was decanted and filtered. The filtrate was evaporated in vacuo and the residue recrystallized from THF. The recrystallized material was combined with the filter cake and dissolved in a hot mixture of 25 ml of 10% HCl and 175 ml of $H_2O$. The hot solution was filtered through a pad of diatomaceous earth, then chilled in ice. The resulting crystals were filtered, washed with a minimum of ice $H_2O$ and dried in air. Further drying in vacuo (50° C., 5 mm Hg) to constant weight afforded 10.70 g (62%) of pure N-(2,6-dibromo-4-fluorophenyl)-N'-(1,4,5,6-tetrahydropyrimidin-2-yl)urea monohydrochloride; m.p. 221°–223° C. dec.; IR(KBr) 3242, 1705, 1676, 1639 cm$^{-1}$; UV max. (MeOH) 277 infl ($\epsilon$1,000) and 228 nm ($\epsilon$27,900).

ANAL. Calcd. for $C_{11}H_{11}Br_2FN_4O·HCl$: C, 30.69; H, 2.81; N, 13.01. FOUND: C, 30.80; H, 2.61; N, 13.01.

EXAMPLE V

N-(2-Chloro-6-Methylphenyl)-N'-(1,4,5,6-Tetrahydropyrimidin-2-yl)urea Monohydrochloride Hemihydrate A mixture of 8.14 g (0.060 mol) of 2-amino-1,4,5,6-tetrahydropyrimidine hydrochloride, 6.0 g (0.075 mol) of 50% NaOH and 75 ml of THF was stirred for 0.5 hours at room temperature and then 15 g $Na_2SO_4$ was added. After stirring for 0.5 hours, a solution of 6.70 g (0.040 mol) of 2-chloro-6-methylphenyl isocyanate in 50 ml of THF was added over a period of 0.5 hours. After stirring for 1 hour, the reaction mixture was filtered, the filtrate evaporated in vacuo and the residue dissolved in 25 ml of 10% HCl and 25 ml of $H_2O$ with warming. After filtration through diatomaceous earth chilling in ice gave the crystalline hydrochloride which was recrystallized from cold $H_2O$ after treatment with charcoal affording 7.15 g (59%). This material was dried in vacuo (20° C., 5 mm Hg) to constant weight to give 7.11 g (59%) of pure N-(2-chloro-6-methylphenyl)-N'-(1,4,5,6-tetrahydropyrimidin-2-yl)urea monohydrochloride hemihydrate, m.p. (190) 215°–220° C. melts, then forms a new solid; m.p. 243°–245° C.; IR($CHCl_3$) 3224, 1713, 1677, 1641, 1543 cm$^{-1}$; UV max. (MeOH) 236 ($\epsilon$16,200) and 217 nm infl ($\epsilon$21,500).

ANAL. Calcd. for $C_{12}H_{15}ClN_4O·HCl·0.5H_2O$: C, 46.17; H, 5.49; N, 17.94; $H_2O$, 2.89. FOUND: C, 46.21; H, 5.53; N, 17.75; $H_2O$, 3.14.

EXAMPLE VI

According to the teachings of Examples I–V, the following compounds are prepared:

1. N-(2,6-Dimethoxyphenyl)-N'-(1,4,5,6-tetrahydropyrimidin-2-yl)urea and its monohydrochloride hydrate; m.p. 176°–178° C. dec.; 210°–212° C.

2. N-(2-Chloro-6-trifluoromethylphenyl)-N'-(1,4,5,6-tetrahydropyrimidin-2-yl)urea and acid addition salts (solvates, hydrates).

3. N-(2,6-bis-Trifluoromethylphenyl)-N'-(1,4,5,6-tetrahydropyrimidin-2-yl)urea and acid addition salts.

4. N-(2-Methyl-6-trifluoromethylphenyl)-N'-(1,4,5,6-tetrahydropyrimidin-2-yl)urea and acid addition salts.

5. N-(2,6-Dibromophenyl)-N'-(1,4,5,6-tetrahydropyrimidin-2-yl)urea and acid addition salts.

6. N-(2,6-Difluorophenyl)-N'-(1,4,5,6-tetrahydropyrimidin-2-yl)urea and acid addition salts.

7. N-(2-Bromo-6-chlorophenyl)-N'-(1,4,5,6-tetrahydropyrimidin-2-yl)urea and acid addition salts.

8. N-(2-Chloro-6-fluorophenyl)-N'-(1,4,5,6-tetrahydropyrimidin-2-yl)urea and acid addition salts.

9. N-(2-Bromo-6-methylphenyl)-N'-(1,4,5,6-tetrahydropyrimidin-2-yl)urea and acid addition salts.

10. N-(2-Chloro-6-methoxyphenyl)-N'-(1,4,5,6-tetrahydropyrimidin-2-yl)urea and acid addition salts.

The following examples illustrate the novel pharmaceutical compositions but are not to be construed as limiting:

EXAMPLE VII 1,000 hard gelatin capsules, each containing 200 milligrams of N-(2,6-dichlorophenyl)-N'-(1,4,5,6-tetrahydropyrimidin-2-yl)urea are prepared from the following formulation:

|  | Grams |
|---|---|
| N-(2,6-Dichlorophenyl)-N'-(1,4,5,6-tetrahydrophyrimidin-2-yl)urea | 500 |
| Starch | 250 |
| Lactose | 750 |
| Talc | 250 |
| Calcium stearate | 10 |

A uniform mixture of the ingredients is prepared by blending and employed to fill two-piece hard gelatin capsules. The capsules are suitable to be orally administered to hypertensive subjects to reduce blood pressure.

EXAMPLE VIII

Gelatin capsules are prepared as described in Example VII, except that in the formulation, 325 grams of N-(2,6-dimethylphenyl)-N'-(1,4,5,6-tetrahydropyrimidin-2-yl)urea is employed as active agent providing capsules containing 325 milligrams of N-(2,6-dimethylphenyl)-N'-(1,4,5,6-tetrahydropyrimidin-2-yl)urea.

EXAMPLE IX 1,000 compressed tablets, each containing 500 milligrams of N-(1,4,5,6-tetrahydropyrimidin-2-yl)urea-N'-(2-trifluoromethylphenyl)urea are prepared from the following formulation.

|  | Grams |
|---|---|
| N-(2,6-dimethylphenyl)-N'-(1,4,5,6-tetrahydropyrimidin-2-yl)urea | 500 |
| Starch | 750 |
| Dibasic calcium phosphate hydrous | 5,000 |
| Calcium stearate | 2.5 |

The finely powdered ingredients are mixed well and granulated with 10 percent starch paste. The granulation is dried and compressed into tablets using starch as a disintegrant and calcium stearate as a lubricant.

EXAMPLE X

Tablets are prepared as described in Example IX, except that N-(2,6-dibromophenyl)-N'-(1,4,5,6-tetrahydropyrimidin-2-yl)urea is employed as active agent.

EXAMPLE XI

Gelatin capsules are prepared as described in Example VII, except that N-(2-chloro-6-methylphenyl)-N'-(1,4,5,6-tetrahydropyrimidin-2-yl)urea is employed as active agent.

I claim:

1. A method which comprises administering to a hypertensive animal, a therapeutically-effective antihypertensive amount of a compound selected from the group consisting of (a) an N-(phenyl)-N'-(1,4,5,6-tetrahydropyrimidin-2-yl)urea having the formula:

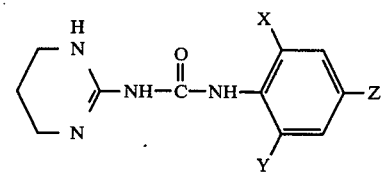

wherein Z is H or F; X and Y are each independently selected from the group consisting of Br, Cl, F, $CH_3$, $CF_3$ and $OCH_3$; and (b) a pharmaceutically-acceptable salt thereof.

2. A method of reducing arterial pressure in hypertensive subjects which comprises administering to said hypertensive subject from about 1 to 500 milligrams per unit dose of an N-(phenyl)-N'-(1,4,5,6-tetrahydropyrimidin-2-yl)urea compound represented by the formula:

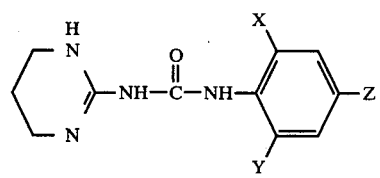

wherein Z is H; X and Y are each independently selected from the group consisting of Br, Cl, $CH_3$ and $CF_3$; and pharmaceutically-acceptable salts thereof.

3. A method according to claim 2, in which the urea compound is N-(2,6-dichlorophenyl)-N'-(1,4,5,6-tetrahydropyrimidin-2-yl)urea; and pharmaceutically-acceptable salts thereof.

4. A method according to claim 2, in which the urea compound is N-(2,6-dimethylphenyl)-N'-(1,4,5,6-tetrahydropyrimidin-2-yl)urea; and pharmaceutically-acceptable salts thereof.

5. A method according to claim 2, in which the urea compound is N-(2,6-dibromophenyl)-N'-(1,4,5,6-tetrahydropyrimidin-2-yl)urea; and pharmaceutically-acceptable salts thereof.

6. A method according to claim 2, in which the urea compound is N-(2-chloro-6-methylphenyl)-N'-(1,4,5,6-tetrahydropyrimidin-2-yl)urea; and pharmaceutically-acceptable salts thereof.

* * * * *